(12) United States Patent
Ookita et al.

(10) Patent No.: US 12,385,848 B2
(45) Date of Patent: Aug. 12, 2025

(54) MARKING INSPECTION DEVICE AND MARKING DEVICE FOR TRANSPARENT EDIBLE OBJECTS

(71) Applicant: QUALICAPS CO., LTD., Yamatokoriyama (JP)

(72) Inventors: Kousuke Ookita, Yamatokoriyama (JP); Kazuaki Matsutani, Yamatokoriyama (JP); Junsuke Yasui, Yamatokoriyama (JP)

(73) Assignee: QUALICAPS CO., LTD., Yamatokoriyama (JP)

( * ) Notice: Subject to any disclaimer, the term of this patent is extended or adjusted under 35 U.S.C. 154(b) by 103 days.

(21) Appl. No.: 18/264,972

(22) PCT Filed: Feb. 7, 2022

(86) PCT No.: PCT/JP2022/004665
§ 371 (c)(1),
(2) Date: Aug. 10, 2023

(87) PCT Pub. No.: WO2022/176672
PCT Pub. Date: Aug. 25, 2022

(65) Prior Publication Data
US 2024/0053277 A1    Feb. 15, 2024

(30) Foreign Application Priority Data
Feb. 16, 2021    (JP) .................................. 2021-022543

(51) Int. Cl.
*G01N 21/88*    (2006.01)
*G01N 21/95*    (2006.01)
(Continued)

(52) U.S. Cl.
CPC ..... *G01N 21/8806* (2013.01); *G01N 21/9508* (2013.01); *G01N 21/958* (2013.01);
(Continued)

(58) Field of Classification Search
CPC ........... G01N 21/8806; G01N 21/9508; G01N 21/958; G01N 33/02; G01N 33/15;
(Continued)

(56) References Cited

U.S. PATENT DOCUMENTS

| | | | |
|---|---|---|---|
| 2013/0058550 A1* | 3/2013 | Tanimoto | G01N 21/9508 382/128 |
| 2016/0180515 A1* | 6/2016 | Seo | A23P 20/00 382/110 |
| 2017/0352149 A1* | 12/2017 | Franchi | G06T 7/593 |

FOREIGN PATENT DOCUMENTS

| | | |
|---|---|---|
| JP | H07-151694 A | 6/1995 |
| JP | H08-271433 A | 10/1996 |

(Continued)

*Primary Examiner* — Michael E Teitelbaum
(74) *Attorney, Agent, or Firm* — Muncy, Geissler, Olds & Lowe, P.C.

(57) ABSTRACT

A marking inspection device 100 for transparent edible objects includes: a conveying unit 2 that conveys, along a linear conveyance path 2a, a transparent edible object C on which a marking pattern has been formed; an inspecting imaging unit 30 that captures an image of the transparent edible object C being conveyed on the conveyance path 2a, and obtains inspecting imaging data; and a control unit that determines quality of the marking pattern, on the basis of the inspecting imaging data 30. In the marking inspection device 100, the inspecting imaging unit 30 includes: a camera 31 disposed so that the imaging direction is orthogonal to the conveyance path 2a; a reflective illuminating unit 32 disposed on a same side of the conveyance path 2a as the camera 31; and a transmissive illuminating unit 33 disposed on an opposite side of the conveyance path 2a from the camera 31.

12 Claims, 5 Drawing Sheets

(51) Int. Cl.
  *G01N 21/958*  (2006.01)
  *G01N 33/02*   (2006.01)
  *G01N 33/15*   (2006.01)
  *G06T 7/00*    (2017.01)

(52) U.S. Cl.
  CPC .... *G06T 7/0006* (2013.01); *G01N 2021/8848* (2013.01); *G01N 33/02* (2013.01); *G01N 33/15* (2013.01); *G06T 2207/30128* (2013.01)

(58) Field of Classification Search
  CPC ..... G01N 2021/8848; G01N 2021/845; G01N 21/85; G01N 21/8851; G01N 21/95607; G01N 2021/8854; G01N 2021/888; G01N 2201/1042; G06T 7/0006; G06T 2207/30128
  See application file for complete search history.

(56) References Cited

FOREIGN PATENT DOCUMENTS

| | | |
|---|---|---|
| JP | H10-282014 A | 10/1998 |
| JP | 2002-071573 A | 3/2002 |
| JP | 2012-234081 A | 11/2012 |
| JP | 6402105 B2 | 10/2018 |
| JP | 2018-186962 A | 11/2018 |
| WO | 2015008742 A1 | 1/2015 |

\* cited by examiner

MARKING INSPECTION DEVICE AND MARKING DEVICE FOR TRANSPARENT EDIBLE OBJECTS

TECHNICAL FIELD

The present invention relates to a marking inspection device and a marking device for transparent edible objects.

BACKGROUND ART

There are known devices capable of marking edible objects such as medicine or food, like a configuration disclosed in Patent Literature 1, for example. Such a marking device includes: a conveying means that conveys an edible object such as a tablet or a capsule: a detecting means that captures an image of the edible object, to obtain direction data; a marking means that forms a marking pattern on the edible object; and a marking inspecting means that inspects the marking pattern formed on the edible object. The marking inspecting means includes an illuminating unit and an imaging unit, and is designed to perform reflective illumination with the illuminating unit from the same side as the imaging unit when the imaging unit images an edible object.

CITATION LIST

Patent Literature

Patent Literature 1: JP 6402105 B2

SUMMARY OF INVENTION

Technical Problem

In the conventional marking device described above, to determine whether marking in accordance with the orientation of an edible object is correctly performed, direction data such as a contour line or a split line of the edible object, and information of the marking pattern formed on the edible object are necessary. However, in a case where the edible object is a transparent edible object having translucency, it might be difficult to obtain these pieces of information with accuracy.

In view of the above, the present invention aims to provide a marking inspection device for transparent edible objects capable of accurately inspecting a marking pattern formed on a transparent edible object, and a marking device including the marking inspection device for transparent edible objects.

Solution to Problem

The above objective of the present invention can be achieved with a marking inspection device for transparent edible objects that includes: a conveying unit that conveys, along a linear conveyance path, a transparent edible object on which a marking pattern has been formed; an inspecting imaging unit that captures an image of the transparent edible object being conveyed on the conveyance path, and obtains inspecting imaging data; and a control unit that determines quality of the marking pattern, on the basis of the inspecting imaging data. The inspecting imaging unit includes: a camera disposed so that the imaging direction is orthogonal to the conveyance path; a reflective illuminating unit disposed on a same side of the conveyance path as the camera; and a transmissive illuminating unit disposed on the opposite side of the conveyance path from the camera.

In this marking inspection device for transparent edible objects, the reflective illuminating unit preferably includes: a ring light; a first polarizing plate that is disposed between the ring light and the conveyance path; and a second polarizing plate that is disposed between the camera and the conveyance path, and has a polarizing axis orthogonal to the polarizing axis of the first polarizing plate. The reflective illuminating unit preferably further includes a polarizing plate driving unit that moves the second polarizing plate.

The control unit preferably performs transmissive illumination with the transmissive illuminating unit in a case where the transparent edible object is colorless and transparent, and performs reflective illumination with the reflective illuminating unit in a case where the transparent edible object is colored and transparent.

The control unit preferably extracts a marking region in accordance with the posture of the capsule specified by the contour of the capsule in the inspecting imaging data, extracts marking pattern data from the marking region, and compares the marking pattern data with reference pattern data to determine quality of the marking pattern.

The above objective of the present invention can also be achieved with a transparent edible object marking device that includes the marking inspection device for transparent edible objects described above, and the transparent edible object marking device further includes a marking unit that forms a marking pattern on a transparent edible object being conveyed on the conveyance path on the upstream side in the conveying direction of the inspecting imaging unit.

The marking unit preferably performs marking by emitting laser light.

Advantageous Effects of Invention

According to the present invention, it is possible to provide a marking inspection device for transparent edible objects capable of accurately inspecting a marking pattern formed on a transparent edible object, and a marking device including the marking inspection device for transparent edible objects.

DESCRIPTION OF EMBODIMENTS

Figure 1:
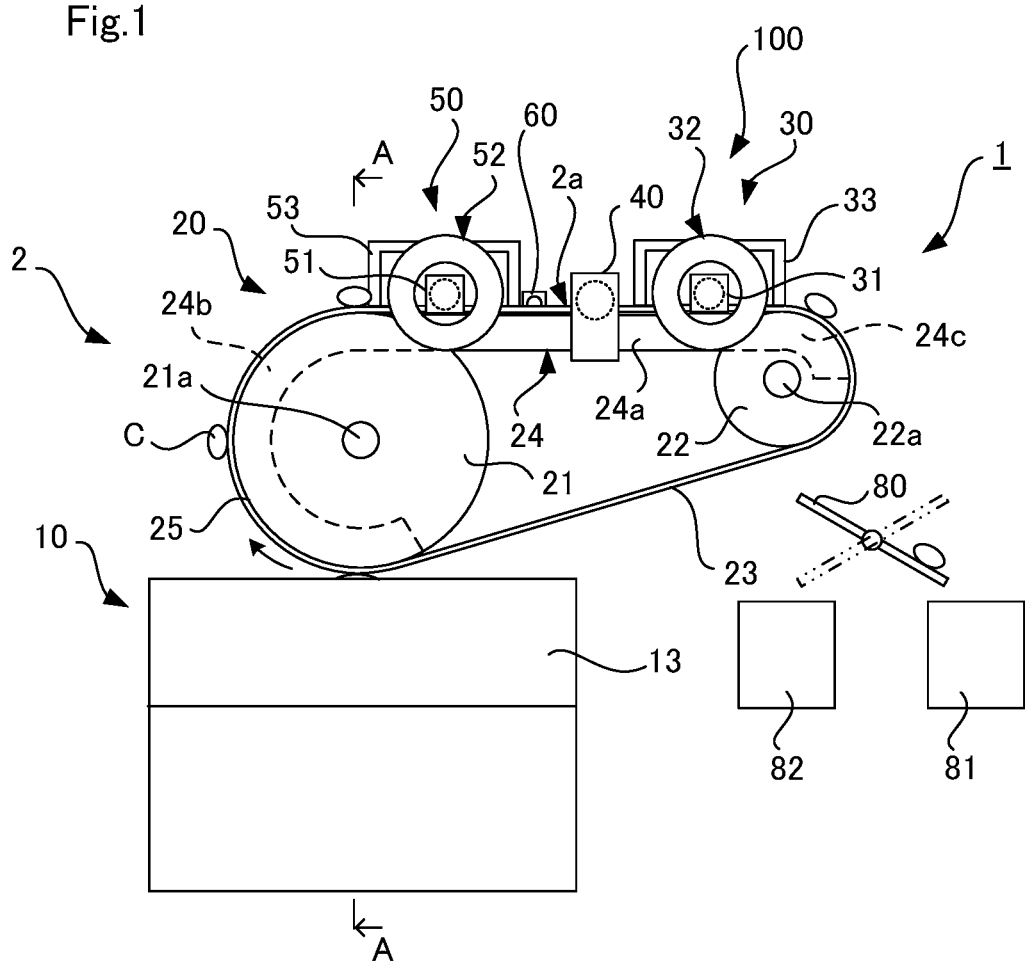
FIG. 1 is a schematic front view of a transparent edible object marking device according to an embodiment of the present invention.

The following is a description of embodiments of the present invention, with reference to the accompanying drawings. FIG. 1 is a schematic front view of a transparent edible object marking device (hereinafter simply referred to as the "marking device") according to an embodiment of the present invention. As illustrated in FIG. 1, the marking device 1 includes a marking inspection device for transparent edible objects (hereinafter simply referred to as the "marking inspection device") 100 that inspects a marking pattern formed on a transparent edible object. The marking inspection device 100 includes a conveying unit 2 and an inspecting imaging unit 30. A transparent edible object is a soft capsule, a hard capsule, solid food, or the like having transparency, and may be either colorless and transparent, or colored and transparent. In this embodiment, a transparent edible object formed with a transparent capsule is described as an example.

Figure 2:
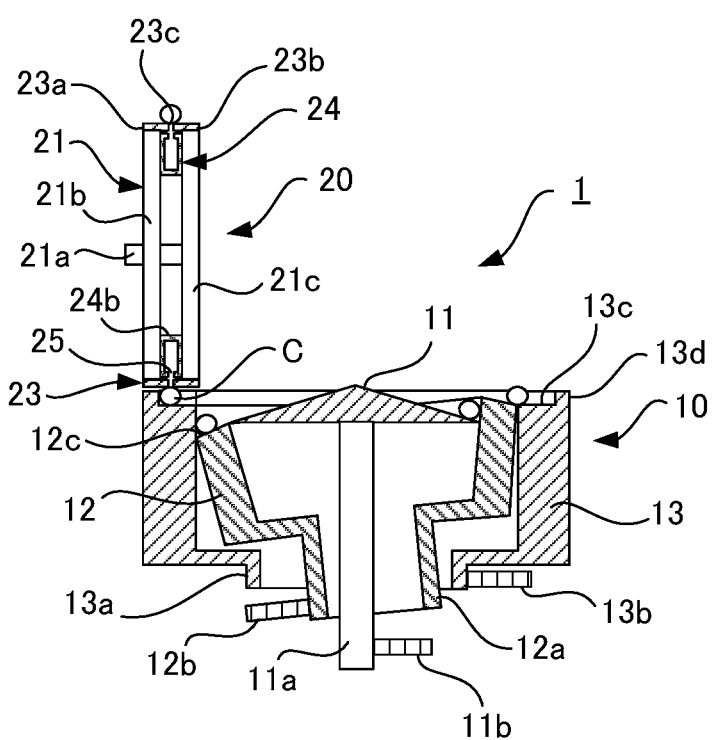
FIG. 2 is a cross-sectional view taken along the line A-A defined in FIG. 1.
Figure 3:
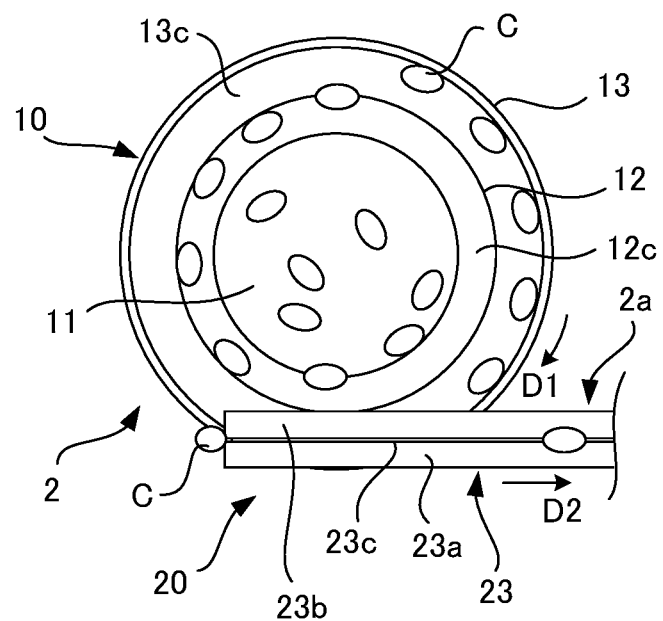
FIG. 3 is a plan view of a relevant portion of the transparent edible object marking device shown in FIG. 1.

FIG. 2 is a cross-sectional view taken along the line A-A defined in FIG. 1. FIG. 3 is a plan view of a relevant portion of the conveying unit 2 shown in FIG. 1. As shown in FIGS. 1 to 3, the conveying unit 2 includes a first conveying device 10 and a second conveying device 20. The first conveying device 10 includes a shade-like disk 11, an intermediate ring 12 that accommodates the disk 11, and a rotating ring 13 that accommodates the intermediate ring 12.

While the rotating shafts 11a and 13a of the disk 11 and the rotating ring 13 extend in a vertical direction, the rotating shaft 12a of the intermediate ring 12 is disposed so as to be slightly tilted with respect to the rotating shafts 11a and 13a. The rotating shafts 11a, 12a, and 13a are connected to driving sources (not shown) such as motors individually provided via decelerators 11b, 12b, and 13b, respectively, and can rotationally drive the disk 11, the intermediate ring 12, and the rotating ring 13, independently of one another.

Conveyance surfaces 12c and 13c are circumferentially formed on the intermediate ring 12 and the rotating ring 13, respectively. The radially outer side of the conveyance surface 13c of the rotating ring 13 is covered with a ring-like protrusion 13d.

The second conveying device 20 includes: a first pulley 21 and a second pulley 22 that have the respective rotating shafts 21a and 22a disposed horizontally; an endless belt member 23 wound around the first pulley 21 and the second pulley 22; and a guide member 24 disposed in the conveying direction of the belt member 23. The diameter of the second pulley 22 is smaller than the diameter of the first pulley 21. The linear portion of the belt member 23 located between the first pulley 21 and the second pulley 22 is horizontally disposed above the first pulley 21 and the second pulley 22, to form a linear conveyance path 2a. On the other hand, the linear portion of the belt member 23 is tilted under the first pulley 21 and the second pulley 22.

As shown in FIG. 2, the first pulley 21 includes two circular plates 21b and 21c joined by the rotating shaft 21a, with a space being left between the two circular plates. Like the first pulley 21, the second pulley 22 also includes two circular plates joined by the rotating shaft 22a, with a space being left between the two circular plates. In this embodiment, the first pulley 21 is a driving pulley connected to a driving motor (not shown), and the second pulley 22 is a driven pulley. However, the first pulley 21 may be a driven pulley, and the second pulley 22 may be a driving pulley.

The belt member 23 includes two band-like conveying belts 23a and 23b, and the respective conveying belts 23a and 23b are wound around the respective circular plates 21b and 21c of the first pulley 21. Between the two conveying belts 23a and 23b, an opening 23c that is a narrow gap is formed over the entire circumference of the belt member 23. The conveying belts 23a and 23b can be formed with flat belts of a soft material such as silicone rubber, for example, but may be formed with V-belts, toothed belts, or the like.

As shown in FIG. 1, the guide member 24 includes: a linear portion 24a that is disposed immediately below the vicinity of the belt member 23 extending horizontally along the conveyance path 2a between the first pulley 21 and the second pulley 22; and arcuate portions 24b and 24c provided on both sides of the linear portion 24a in the conveying direction. Each of the arcuate portions 24b and 24c is inserted between the two circular plates of each corresponding one of the first pulley 21 and the second pulley 22, and is curved in an arcuate shape along the belt member 23 wound around the first pulley 21 and the second pulley 22.

As shown in FIG. 2, the guide member 24 is formed in a hollow cylindrical shape, and a slit-like suctioning portion 25 is formed along the opening 23c in a portion where the guide member 24 faces the opening 23c of the belt member 23. The inside of the guide member 24 can be decompressed by an operation of a vacuum pump (not shown), and a capsule C is attracted to the suctioning portion 25 via the opening 23c of the belt member 23, so that the capsule C attracted to the belt member 23 can be conveyed together with the belt member 23. The opening 23c of the belt member 23 of this embodiment is continuously formed between the two conveying belts 23a and 23b in the longitudinal direction. However, the belt member 23 may be formed as a single band-like belt, and openings having a circular shape, an elliptical shape, or a slit-like shape may be intermittently formed in the longitudinal direction of the band-like belt.

Figure 4:
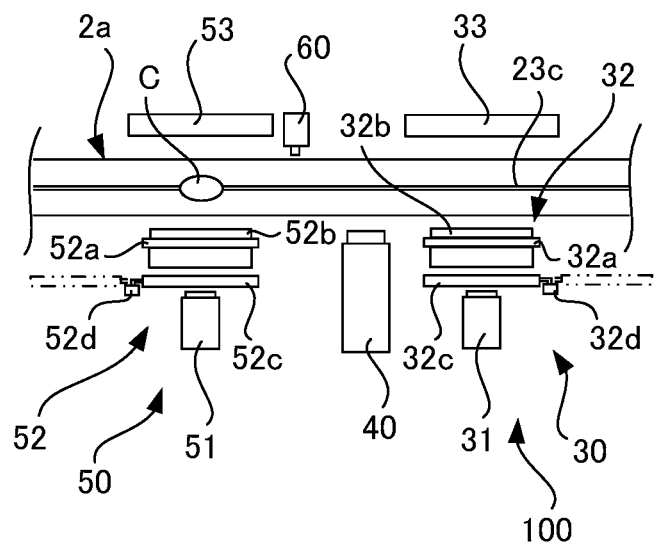
FIG. 4 is a plan view of another relevant portion of the transparent edible object marking device shown in FIG. 1.

FIG. 4 is an enlarged plan view of a portion in the vicinity of the conveyance path 2a shown in FIG. 1. As shown in FIG. 4, the inspecting imaging unit 30 includes a camera 31, a reflective illuminating unit 32, and a transmissive illuminating unit 33. The camera 31 is formed with a CCD area camera, a CCD line camera, or the like, is disposed so that the imaging direction becomes orthogonal to the conveyance path 2a in a plan view, and horizontally images a capsule C being conveyed on the conveyance path 2a along the upper surface of the belt member 23. The imaging direction of the camera 31 is preferably substantially parallel to the upper surface of the belt member 23. However, in a case where the lowermost portion of the capsule C is in the opening 23c of the belt member 23, imaging may be performed obliquely downward from above the belt member 23. As an example, the angle between the imaging direction of the camera 31 and the upper surface of the belt member 23 can be set within the range of 0 to 15 degrees.

The reflective illuminating unit 32 is disposed on the same side of the conveyance path 2a as the camera 31, and illuminates the capsule C with a white LED or the like from the same side as the camera 31. The reflective illuminating unit 32 of this embodiment includes a ring light 32a capable of uniformly illuminating the capsule C from the entire circumference, a first polarizing plate 32b, and a second polarizing plate 32c. The illuminating light of the ring light 32a may be infrared light or the like, other than visible light.

The first polarizing plate 32b is formed in a ring-like shape, is disposed in the vicinity of the ring light 32a, and is interposed between the ring light 32a and the conveyance path 2a, so that the capsule C is illuminated with linearly polarized light emitted from the ring light 32a. The second polarizing plate 32c is disposed in the vicinity of the camera 31 so as to cover the lens portion of the camera 31, and is interposed between the camera 31 and the conveyance path 2a, so that surface-reflected light from the capsule C passes therethrough and is observed by the camera 31. The second polarizing plate 32c is disposed so that the polarizing axis becomes orthogonal to the polarizing axis of the first polarizing plate 32b. The second polarizing plate 32c is designed to be movable with a polarizing plate driving unit 32d such as an actuator. As the driving axis of the polarizing plate driving unit 32d rotates, the second polarizing plate 32c can be retracted from the front of the camera 31 as indicated by a dash-dot-dot-dash line in FIG. 4. The polarizing plate driving unit 32d may be designed to linearly move the second polarizing plate 32c and retract the second polarizing plate 32c from the front of the camera 31.

The transmissive illuminating unit 33 is disposed on the opposite side of the conveyance path 2a from the camera 31, and illuminates the capsule C with a white LED or the like from the opposite side to the camera 31. The transmissive illuminating unit 33 of this embodiment is a surface light source in which a plurality of light emitting elements is arranged in a matrix. The illuminating light of the transmissive illuminating unit 33 may be infrared light or the like, other than visible light.

Figure 5:
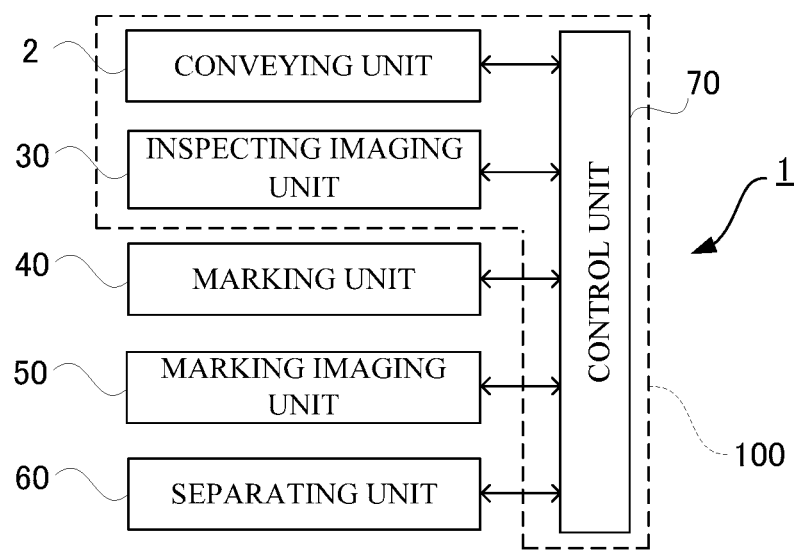
FIG. 5 is a block diagram of the transparent edible object marking device shown in FIG. 1.

As shown in a block diagram in FIG. 5, operations of the conveying unit 2 and the inspecting imaging unit 30 in the marking inspection device 100 are controlled by a control unit 70.

As shown in FIGS. 1 to 5, the marking device 1 of this embodiment includes a marking unit 40, a marking imaging unit 50, and a separating unit 60, in addition to the marking inspection device 100 described above. The marking unit 40, the marking imaging unit 50, and the separating unit 60 are provided on the upstream side in the conveying direction of the inspecting imaging unit 30 in the vicinity of the conveyance path 2a. Operations of the marking unit 40, the marking imaging unit 50, and the separating unit 60 are controlled by the control unit 70.

The marking unit 40 is a laser marking device, and can perform marking by laser-spot scanning the surface of the capsule C conveyed to a predetermined position and thus thermally denaturing the surface of the capsule C. The type of the laser light of the marking unit 40 is preferably carbon dioxide ($CO_2$) laser light suitable for performing marking on a transparent edible object, for example, but may be some other laser light capable of forming a marking on the surface of a transparent material. For example, in the case of a transparent edible object in which at least one discoloration inducing oxide selected from the group consisting of titanium oxide, yellow ferric oxide, and red ferric oxide is dispersed, the type of the laser light may also be UV laser light. The marking unit 40 is preferably capable of performing marking in accordance with the posture of the capsule C without moving or rotating the capsule C, by transforming coordinate data in a reference coordinate system into coordinate data in a machining coordinate system.

The marking imaging unit 50 is disposed on the upstream side of the marking unit 40 in the conveying direction, and includes a camera 51, a reflective illuminating unit 52, and a transmissive illuminating unit 53, like the inspecting imaging unit 30. The reflective illuminating unit 52 includes a ring light 52a, a first polarizing plate 52b, a second polarizing plate 52c, and a polarizing plate driving unit 52d. The configurations and positions of the respective components of the marking imaging unit 50 are similar to the configurations and positions of the respective components of the inspecting imaging unit 30, and therefore, detailed explanation thereof is not made herein.

The separating unit 60 is disposed between the marking imaging unit 50 and the marking unit 40 in the vicinity of the conveyance path 2a, and can selectively separate the capsule C from the conveyance path 2a by injecting compressed air to the capsule C being conveyed on the conveyance path 2a. The separating unit 60 is not limited to any particular configuration, and may be a pusher or the like that physically pushes the capsule C on the conveyance path 2a to separate the capsule C from the conveyance path 2a, for example. The capsule C separated from the conveyance path 2a by the operation of the separating unit 60 falls directly or via a chuter (not shown) onto the first conveying device 10 disposed below the conveyance path 2a, and is conveyed again toward the conveyance path 2a.

Next, operations of the marking device 1 having the above configuration are described. When a plurality of capsules C is supplied onto the disk 11 while the disk 11, the intermediate ring 12, and the rotating ring 13 of the first conveying device 10 are being rotationally driven in the same direction, the capsules C are subjected to centrifugal force, and move onto the conveyance surface 13c of the rotating ring 13 via the conveyance surface 12c of the intermediate ring 12. In this manner, the capsules C can be arranged in a line on the conveyance surface 13c, and these capsules C can be conveyed in the direction of rotation of the rotating ring 13 (the direction indicated by an arrow D1 in FIG. 3). The rotational speeds of the disk 11, the intermediate ring 12, and the rotating ring 13 are preferably set so that the rotational speed of the disk 11 becomes the lowest, and the rotational speed of the rotating ring 13 becomes the highest. In this manner, reliable aligned conveyance of the capsules C by the rotating ring 13 can be facilitated.

The first conveying device 10 is only required to align the capsules C on the conveyance surface 13c of the rotating ring 13 and convey the capsules C in the direction of rotation of the rotating ring 13. For example, without the intermediate ring 12 being provided, the respective rotating shafts of the disk 11 and the rotating ring 13 may be tilted with respect to each other, and the capsules C supplied onto the disk 11 may be directly moved onto the conveyance surface 13c of the rotating ring 13. The rotating shaft 13a of the rotating ring 13 is preferably disposed in the vertical direction as in this embodiment, but is only required to be disposed to extend in the vertical direction. For example, the rotating shaft 13a may be slightly tilted with respect to the vertical direction.

The capsules C aligned and conveyed toward the second conveying device 20 by the first conveying device 10 are sequentially attracted to the belt member 23 in the vicinity of a lower portion of the first pulley 21 by the suctioning portion 25, and are linearly conveyed in the direction indicated by an arrow D2 in FIG. 3 over the first pulley 21 and the second pulley 22, while remaining in the attracted state. In this manner, the capsules C aligned by the first conveying device 10 are conveyed along the linear conveyance path 2a, while being made to maintain the aligned state by the second conveying device 20.

At the position of transfer of the capsules C from the rotating ring 13 to the belt member 23, the direction of conveyance by the rotating ring 13 and the direction of conveyance by the belt member 23 are preferably the same as each other as in this embodiment. With such arrangement, the transfer of the capsules C can be reliably performed. Further, by making the speed of conveyance of the capsules C by the belt member 23 higher than the speed of conveyance of the capsules C by the rotating ring 13, it is possible to widen the alignment pitch of the capsules C being aligned and conveyed by the belt member 23.

When a capsule C being conveyed on the conveyance path 2a passes through the marking imaging unit 50, a side surface of the capsule C is imaged, and thus, marking imaging data is obtained. On the basis of the marking imaging data, the control unit 70 sets a marking region on the capsule C, and performs marking by controlling the operation of the marking unit 40. In the marking unit 40, coordinate data in the reference coordinate system of a marking pattern formed with a character, a number, a symbol, a figure, or the like, or a combination thereof is stored beforehand in a memory. The control unit 70 transforms the coordinate data in the reference coordinate system into coordinate data in the machining coordinate system so that a marking pattern is formed along the marking region that has been set in accordance with the posture of the capsule C. The control unit 70 then performs drive control on the laser spot of the marking unit 40 in the machining coordinate system.

The capsule C on which the marking pattern has been formed is conveyed along the conveyance path 2a toward the inspecting imaging unit 30. When the capsule C passes through the inspecting imaging unit 30, the side surface including the marking region is imaged, and thus, inspecting imaging data is obtained. On the basis of the inspecting imaging data, the control unit 70 determines the quality of the marking pattern in the marking region.

Figure 6:
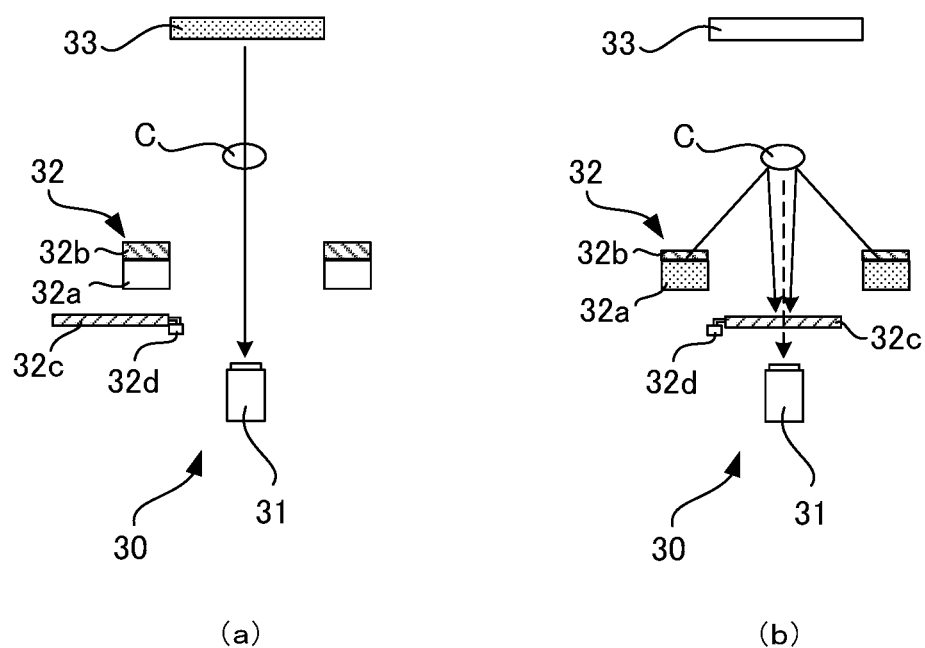
FIG. 6 is a diagram for explaining an operation of the transparent edible object marking device shown in FIG. 1.

In a case where the capsule C passing through the inspecting imaging unit 30 is colorless and transparent, the control unit 70 turns on the transmissive illuminating unit 33 but turns off the reflective illuminating unit 32, and thus illuminates the capsule C with the transmissive illuminating unit 33, as shown in FIG. 6(*a*). The term "colorless and transparent" in this specification is not necessarily limited to completely colorless and transparent, and also includes cases where transparency is sufficiently high though the object is slightly colored, and cases where the object is semi-transparent. Since part of the illuminating light of the transmissive illuminating unit 33 is transmitted through the capsule C and enters the camera 31, the contour of the capsule C appears because of refraction of light, and the portion corresponding to the marking pattern formed on the surface of the capsule C appears as a shadow in the inspecting imaging data. In a case where illumination is performed by the transmissive illuminating unit 33, to prevent a decrease in the quantity of illuminating light, it is preferable to operate the polarizing plate driving unit 32d and retract the second polarizing plate 32c from the front of the camera 31.

On the other hand, in a case where the capsule C is colored and transparent, the control unit 70 turns on the reflective illuminating unit 32 but turns off the transmissive illuminating unit 33, and thus illuminates the capsule C with the reflective illuminating unit 32, as shown in FIG. 6(*b*). The illuminating light emitted from the ring light 32a of the reflective illuminating unit 32 is turned into linearly polarized light by the first polarizing plate 32b, and illuminates the capsule C. The surface-reflected light from the capsule C then enters the camera 31 through the second polarizing plate 32c. Since the polarizing axis of the second polarizing plate 32c is orthogonal to the polarizing axis of the first polarizing plate 32b, reflection of illuminating light due to regular reflection light from the surface of the capsule C is removed, and only diffusely reflected light is observed by the camera 31. Accordingly, it is possible to effectively reduce the glare on the surface of the colored transparent capsule C, and obtain the inspecting imaging data in which the contour of the capsule C and the marking are clear.

Whether the capsule C is colorless and transparent, or is colored and transparent can be determined by the operator, and be input to the control unit 70. In this case, it is possible to determine whether the capsule C is colorless and transparent, or is colored and transparent by comparing pieces of inspecting imaging data obtained under the respective conditions of reflective illumination by the reflective illuminating unit 32 and transmissive illumination by the transmissive illuminating unit 33. Alternatively, the control unit 70 may be designed to measure the illuminating light transmittance of the capsule C, and automatically determine that the capsule C is colorless and transparent in a case where the illuminating light transmittance is equal to or higher than a threshold, but automatically determine that the capsule C is colored and transparent in a case where the illuminating light transmittance is lower than the threshold.

Figure 7:
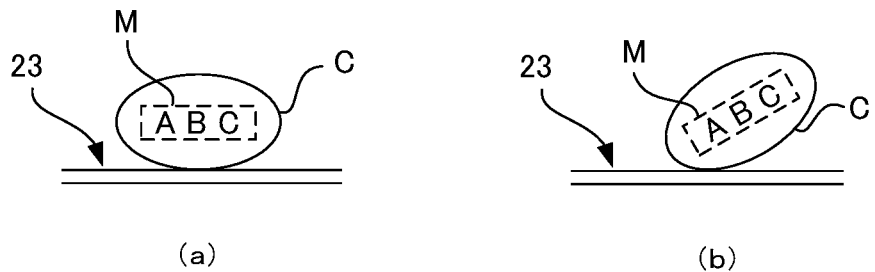
FIG. 7 is a diagram for explaining another operation of the transparent edible object marking device shown in FIG. 1.

The setting of the marking region on a capsule C in inspecting imaging data is performed on the basis of the posture of the capsule C being conveyed on the conveyance path 2a. As shown in FIG. 7(*a*), a capsule C on the belt member 23 is normally attracted to the belt member 23 in the most stable position, but, depending on the location where the capsule C is attracted, the capsule C might be attracted to the belt member 23 in a slightly upright position, as shown in FIG. 7(*b*). The control unit 70 can extract a marking region M corresponding to the posture of the capsule C as shown in FIGS. 7(*a*) and 7(*b*), by storing beforehand the contours and the marking regions corresponding to various postures of capsules C and collating the contours included in the inspecting imaging data. It is also possible to determine the marking region M on the capsule C by comparing the contour of the capsule C included in the inspecting imaging data with a reference contour and calculating the angle of rotation with respect to the reference contour. The posture of a transparent edible object such as the capsule C may be specified on the basis of the position, the orientation, and the like of a portion having a characteristic shape appearing on the surface of the transparent edible object, such as a split line or an engraved mark, other than the contour of the transparent edible object.

Further, in the control unit 70, reference pattern data corresponding to the marking pattern is stored beforehand in a memory unit. The control unit 70 determines the quality of the marking pattern by extracting the marking pattern data from the marking region in the inspecting imaging data and comparing the marking pattern data with the reference pattern data. The method for comparing the marking pattern data with the reference pattern data is not limited to any particular method, and areas, shapes, or the like can be compared, for example.

In a case where the marking pattern data and the reference pattern data are compared with each other in terms of area, for example, a check is made to determine whether the absolute value of the difference between the areas of the two pieces of data is within a threshold. In a case where the absolute value is within the threshold, the marking pattern can be determined to be good. In a case where the absolute value is beyond the threshold, the marking pattern can be determined to be defective. More specifically, pixels having a predetermined luminance or higher from the inside of the image are regarded as a marking with the use of a binarization algorithm, and area comparison can be performed in accordance with the number of extracted pixels. In a case where the marking pattern data and the reference pattern data are compared with each other in terms of shape, for example, a check is made to determine whether the concordance rate is higher than a threshold when the two shapes are overlapped on each other. In a case where the concordance rate is higher than the threshold, the marking pattern can be determined to be good. In a case where the concordance rate is lower than the threshold, the marking pattern can be determined to be defective. More specifically, the contour shape of the marking pattern is registered beforehand through geometric pattern matching, and the quality of the marking pattern can be determined from a concordance rate that is the similarity between a search result image obtained by a model search in the image and a model image. Further, the comparison in terms of area and the comparison in terms of shape can be combined in determining the quality of the marking pattern.

As shown in FIG. 1, the capsules C on which the marking pattern quality determination has been performed are sorted into a non-defective product box 81 and a defective product box 82 by the control unit 70 controlling the operation of a sorting damper 80.

With the marking inspection device 100 of this embodiment, even in a case where a transparent edible object on which a marking pattern has been formed is colorless and transparent, or is colored and transparent, the inspecting imaging unit 30 can obtain inspecting imaging data in which the posture and the marking pattern of the transparent edible object are clear, and thus, the marking pattern can be inspected with high precision.

The illumination condition for the marking imaging unit 50 is preferably the same as the illumination condition for the inspecting imaging unit 30. In a case where reflective illumination is performed by the reflective illuminating unit 32 in the inspecting imaging unit 30, reflective illumination is performed by the reflective illuminating unit 52 in the marking imaging unit 50. In a case where transmissive illumination is performed by the transmissive illuminating unit 33 in the inspecting imaging unit 30, on the other hand, reflective illumination is performed by the transmissive illuminating unit 53 in the marking imaging unit 50. As a result, like the inspecting imaging data, marking imaging data in which the posture of the capsule C is clear can be obtained, and the control unit 70 can set the marking region on the capsule C on the basis of the posture of the capsule C in the marking imaging data.

Meanwhile, there are cases where a seam is present on the surface of a transparent edible object in the form of a capsule. For example, a heat-sealed portion between coating films formed by a rotary method appears as a seam on a soft capsule, and might affect the visibility of the marking.

Figure 8:
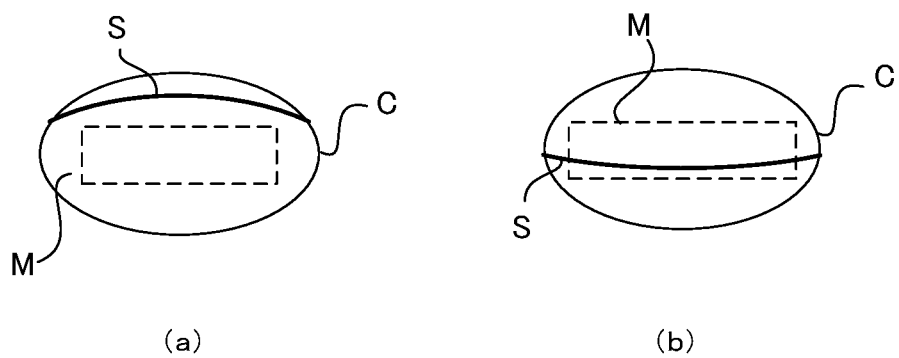
FIG. 8 is a diagram for explaining yet another operation of the capsule marking device shown in FIG. 1.

Therefore, the control unit 70 determines whether a seam is present in the marking region set in the marking imaging data, and, if a seam is present, calculates the size of the seam. The position of a seam on the surface of a capsule C being conveyed on the conveyance path 2a is random. Therefore, in a case where a seam S does not overlap the marking region M as shown in FIG. 8(a), any marking defect problem does not occur. On the other hand, when the seam S overlaps the marking region M as shown in FIG. 8(b), visibility of marking might become lower.

In a case where the size of the seam in the marking region M is equal to or larger than a predetermined reference size that adversely affects the visibility of marking, the control unit 70 operates the separating unit 60 at the timing when the capsule C passes through the separating unit 60, to separate the capsule C from the conveyance path 2a. The capsule C separated from the conveyance path 2a falls onto the first conveying device 10, and is conveyed toward the conveyance path 2a, and the first imaging step is then performed again. The capsule C separated from the conveyance path 2a may be collected in a container or the like, or may be supplied to the first conveying device 10 after a certain amount of capsules C is stored. The size of the seam S in the marking region M can be the proportion of the area of the seam in the marking region M, for example. However, the length, the thickness, or the like of the seam present in the marking region M may be regarded as the size of the seam.

In a case where the size of the seam in the marking region M is smaller than the predetermined reference size, the control unit 70 causes the capsule C to pass without operating the separating unit 60, and performs marking at the timing when the capsule C is conveyed to the marking unit 40. The capsule C on which the marking pattern has been formed is then subjected to the marking pattern inspection by the marking inspection device 100 as described above.

In a case where there are no seams in the marking region, the quality of the marking pattern can be determined on the basis of the inspecting imaging data as described above. However, there is a possibility that a seam of a smaller size than the predetermined reference size might exist in the marking region in the inspecting imaging data. Therefore, the quality of the marking pattern may be determined on the basis of difference data between the marking imaging data obtained by the marking imaging unit 50 and the inspecting imaging data obtained by the inspecting imaging unit 30.

Figure 9:
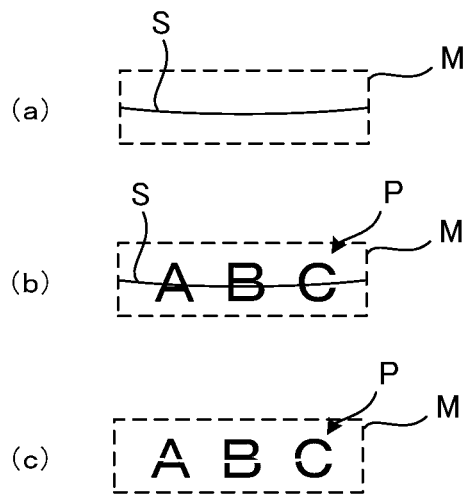
FIG. 9 is a diagram for explaining still another operation of the capsule marking device shown in FIG. 1.

For example, in a case where a seam S of a smaller size than the predetermined reference size is present in the marking region M in the first image data as shown in FIG. 9(a), the control unit 70 removes the marking region M in the marking imaging data shown in FIG. 9(a) from the marking region M in the inspecting imaging data shown in FIG. 9(b), to obtain the difference data of the marking region M shown in FIG. 9(c). In the difference data shown in FIG. 9(c), the portion corresponding to the seam S shown in FIG. 9(a) is missing from a marking pattern P. However, the size of the seam S is smaller than the predetermined reference size that does not adversely affect the visibility of the marking pattern P, and thus, the quality of the marking pattern P can be determined with high precision.

As described above, in a case where the seam S of a capsule C overlaps the marking region M, a check is made to determine whether the seam S is equal to or larger in size than a predetermined reference size. In a case where the seam S is equal to or larger in size than the predetermined reference size, the capsule C can be separated from the conveyance path 2a without any marking pattern formed. Thus, marking with high visibility can be efficiently performed.

REFERENCE SIGNS LIST 1 transparent edible object marking device
2 conveying unit
2a conveyance path
30 inspecting imaging unit
31 camera
32 reflective illuminating unit
32a ring light
32b first polarizing plate
32c second polarizing plate
32d polarizing plate driving unit
33 transmissive illuminating unit
40 marking unit
50 marking imaging unit
60 separating unit 70 control unit
100 marking inspection device for transparent edible objects
C capsule (transparent edible object)
M marking region

The invention claimed is:

1. A marking inspection device for transparent edible objects comprising: a conveying unit that conveys, along a linear conveyance path, a transparent edible object on which a marking pattern has been formed; an inspecting imaging unit that captures an image of the transparent edible object being conveyed on the conveyance path, and obtains inspecting imaging data; and a control unit that determines quality of the marking pattern, on a basis of the inspecting imaging data,
wherein the inspecting imaging unit includes: a camera disposed so that an imaging direction is orthogonal to the conveyance path; a reflective illuminating unit disposed on a same side of the conveyance path as the camera; and a transmissive illuminating unit disposed on an opposite side of the conveyance path from the camera, and
wherein the reflective illuminating unit includes: a ring light; a first polarizing plate that is disposed between the ring light and the conveyance path; and a second polarizing plate that is disposed between the camera and the conveyance path, and has a polarizing axis orthogonal to a polarizing axis of the first polarizing plate.

2. The marking inspection device for transparent edible objects according to claim 1, wherein the reflective illuminating unit further includes a polarizing plate driving unit that moves the second polarizing plate.

3. The marking inspection device for transparent edible objects according to claim 1, wherein the control unit performs transmissive illumination with the transmissive illuminating unit in a case where the transparent edible object is colorless and transparent, and performs reflective illumination with the reflective illuminating unit in a case where the transparent edible object is colored and transparent.

4. The marking inspection device for transparent edible objects according to claim 1, wherein the control unit extracts a marking region in accordance with a posture of the capsule specified by a contour of the capsule in the inspecting imaging data, extracts marking pattern data from the marking region, and compares the marking pattern data with reference pattern data to determine quality of the marking pattern.

5. A transparent edible object marking device comprising the marking inspection device for transparent edible objects according to claim 1,
wherein the transparent edible object marking device further comprises a marking unit that forms a marking pattern on a transparent edible object being conveyed on the conveyance path on an upstream side in a conveying direction of the inspecting imaging unit.

6. The transparent edible object marking device according to claim 5, wherein the marking unit performs marking by emitting laser light.

7. A marking inspection device for transparent edible objects comprising: a conveying unit that conveys, along a linear conveyance path, a transparent edible object on which a marking pattern has been formed; an inspecting imaging unit that captures an image of the transparent edible object being conveyed on the conveyance path, and obtains inspecting imaging data; and a control unit that determines quality of the marking pattern, on a basis of the inspecting imaging data,
wherein the inspecting imaging unit includes: a camera disposed so that an imaging direction is orthogonal to the conveyance path; a reflective illuminating unit disposed on a same side of the conveyance path as the camera; and a transmissive illuminating unit disposed on an opposite side of the conveyance path from the camera, and
wherein the control unit performs transmissive illumination with the transmissive illuminating unit in a case where the transparent edible object is colorless and transparent, and performs reflective illumination with the reflective illuminating unit in a case where the transparent edible object is colored and transparent.

8. The marking inspection device for transparent edible objects according to claim 7, wherein the reflective illuminating unit includes: a ring light; a first polarizing plate that is disposed between the ring light and the conveyance path; and a second polarizing plate that is disposed between the camera and the conveyance path, and has a polarizing axis orthogonal to a polarizing axis of the first polarizing plate.

9. The marking inspection device for transparent edible objects according to claim 7, wherein the reflective illuminating unit further includes a polarizing plate driving unit that moves the second polarizing plate.

10. The marking inspection device for transparent edible objects according to claim 7, wherein the control unit extracts a marking region in accordance with a posture of the capsule specified by a contour of the capsule in the inspecting imaging data, extracts marking pattern data from the marking region, and compares the marking pattern data with reference pattern data to determine quality of the marking pattern.

11. A transparent edible object marking device comprising the marking inspection device for transparent edible objects according to claim 7,
wherein the transparent edible object marking device further comprises a marking unit that forms a marking pattern on a transparent edible object being conveyed on the conveyance path on an upstream side in a conveying direction of the inspecting imaging unit.

12. The transparent edible object marking device according to claim 11, wherein the marking unit performs marking by emitting laser light.

* * * * *